United States Patent
Hasegawa et al.

(10) Patent No.: US 8,182,774 B2
(45) Date of Patent: May 22, 2012

(54) EU(III) COMPLEX AND NANOSIZED EUSE CRYSTAL OBTAINED THEREFROM (75) Inventors: Yasuchika Hasegawa, Nara (JP); Tsuyoshi Kawai, Ikoma (JP); Takaaki Adachi, Ichihara (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 883 days.

(21) Appl. No.: 12/224,499

(22) PCT Filed: Feb. 23, 2007

(86) PCT No.: PCT/JP2007/000118
§ 371 (c)(1),
(2), (4) Date: Aug. 28, 2008

(87) PCT Pub. No.: WO2007/102271
PCT Pub. Date: Sep. 13, 2007

(65) Prior Publication Data
US 2009/0015919 A1 Jan. 15, 2009

(30) Foreign Application Priority Data
Mar. 9, 2006 (JP) ................................. 2006-064890

(51) Int. Cl.
*C01F 17/00* (2006.01)

(52) U.S. Cl. ............... 423/21.1; 359/484.1; 359/484.03; 252/585; 423/263; 423/508

(58) Field of Classification Search .................. None
See application file for complete search history.

(56) References Cited

U.S. PATENT DOCUMENTS 3,353,907 A * 11/1967 Shafer .......................... 423/263
3,371,041 A 2/1968 Holtzberg et al.
(Continued)

FOREIGN PATENT DOCUMENTS
JP A-2001-354417 12/2001
(Continued)

OTHER PUBLICATIONS

T. Adachi, A. Tanaka, Y. Hasegawa, T. Kawai, 'Preparation of EuSe nanoparticles from Eu(III) complex containing selenides', Thin Solid Films, vol. 516, 2008, pp. 2460-2462.*

(Continued)

*Primary Examiner* — Arnel C Lavarias
(74) *Attorney, Agent, or Firm* — Oliff & Berridge, PLC

(57) ABSTRACT

A method to easily manufacture a nanosized EuSe crystal which has been conventionally difficult to be manufactured. Heating an Eu(III) complex whose general formula is represented by the following formula generates an EuSe crystal having a particle size corresponding to the heating condition. Alternatively, the mixture composed of Eu(III) complex, a counter cation, and a solvent may be heated. The particle size of the nanosized EuSe crystals can be manipulated by the heating condition, thus the absorption wavelength of the EuSe crystals can be easily controlled. In addition, it is easy to create a magnetooptic-responsive plastic using the high dispersibility of the EuSe crystals, thus it can be immediately applied to an optical isolator or other devices.

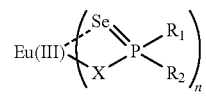

8 Claims, 5 Drawing Sheets

EuSe nanoparticles

U.S. PATENT DOCUMENTS

| | | | | |
|---|---|---|---|---|
| 3,418,036 | A | * | 12/1968 | Holtzberg et al. ............ 359/283 |
| 3,770,422 | A | * | 11/1973 | Darnell ........................... 75/370 |
| 6,972,562 | B1 | * | 12/2005 | Vlasko-Vlasov et al. . 324/244.1 |
| 7,250,117 | B2 | * | 7/2007 | Iwanaga et al. .......... 252/301.16 |
| 2003/0161777 | A1 | | 8/2003 | Yanagida et al. |

FOREIGN PATENT DOCUMENTS

| | | |
|---|---|---|
| JP | A-2004-354927 | 12/2004 |

OTHER PUBLICATIONS

Y. Hasegawa, T. Adachi, A. Tanaka, M. Afzaal, P. O'Brien, T. Doi, Y. Hinatsu, K. Fujita, K. Tanaka, T. Kawai, 'Remarkable magneto-optical properties of europium selenide nanoparticles with wide energy gaps', J. Am. Chem. Soc., vol. 130, 2008, pp. 5710-5715.*

Y. Hasegawa, Y. Okada, T. Kataoka, T. Sakata, H. Mori, Y. Wada, 'Synthesis and photophysical properties of EuS nanoparticles from the thermal reduction of novel Eu(III) complex', J. Phys. Chem. B, vol. 110, 2006, pp. 9008-9011.*

A. Tanaka, T. Adachi, Y. Hasegawa, T. Kawai, 'Crystal growth of nanoscaled europium selenide having characteristic crystal shapes', J. Alloys and Compounds, vol. 488, 2009, pp. 538-540.*

R. Davies, C. Francis, A. Jurd, M. Martinelli, A. White, D. Williams, 'Coordination chemistry of diselenophosphinate complexes: The X-ray single-crystal structures of [K(Se2PPh2)(THF)2]2 and [In(Se2PPh2)3]L (L=THF, PhMe)', Inorganic Chemistry, vol. 43, No. 16, 2004, pp. 4802-4804.*

Kataoka et al.; "Size-controlled synthesis of quantum-sized EuS nanoparticles and tuning of their Faraday rotation peak;" Chem. Commun., Sep. 8, 2005; pp. 6038-6040; The Royal Society of Chemistry.

* cited by examiner

EuSe nanoparticles

Fig. 6

| Observed value (2θ) | Theoretical value (d-space) | Observed value (d-space) | |
|---|---|---|---|
| 25.1200 | 3.5421 | 3.560 | EuSe |
| 29.2480 | 3.0510 | 3.087 | EuSe |
| 41.4760 | 2.1754 | 2.184 | EuSe |

Fig. 7

| | EuSe | | |
|---|---|---|---|
| Observed value (d-space) | Theoretical value (d-space) | hkl | Int |
| | 3.560 | 111 | 30 |
| 3.09 | 3.087 | 200 | 100 |
| 2.24 | 2.184 | 220 | 100 |
| 1.87 | 1.851 | 311 | 30 |
| | 1.783 | 222 | 50 |
| 1.54 | 1.545 | 400 | 30 |
| | 1.381 | 420 | 100 |
| | 1.261 | 422 | 70 |

Fig. 8

EDS of EuSe nanocrystals

EU(III) COMPLEX AND NANOSIZED EUSE CRYSTAL OBTAINED THEREFROM

TECHNICAL FIELD

The present invention relates to a nanosized EuSe crystal and a method for manufacturing the nanosized EuSe crystal.

BACKGROUND ART

Substances having excellent magnetooptical properties such as the Faraday effect and Kerr effect play an important role as a substrate material in the optical information communications field (application example: optical isolator), and as a substrate material in the optical recording field (application example: magnetooptical memory).

As a substance with excellent magnetooptical properties as just described, a crystal such as Bi:YIG is generally used today. However, EuO and EuS which are a nanocrystal using an europium (Eu) ion have been proposed as a substance having better magnetooptical properties. As an example, Patent Document 1 discloses a technique for immobilizing nanocrystals of EuO and EuS in plastic. Since EuO and EuS doped in plastic exhibit the significant Faraday effect, they are expected to be applied to a next-generation isolator.

[Patent Document 1] Japanese Unexamined Patent Application Publication No. 2004-354927

[Non-Patent Document 1] Y. Hasegawa, T. Kataoka et al., "Size-controlled synthesis of quantum-sized EuS nanoparticles and tuning of their Faraday rotation peak," *Chem. Commun.*, 6038 (2005).

DISCLOSURE OF THE INVENTION

Problem to be Solved by the Invention

The existence of EuSe has been known for many years as a magnetooptical material having a capability higher than that of EuO and EuS which have excellent magnetooptical properties as described earlier. However, there have been no case to date which has reported that EuSe has been nanosized.

In order to manufacture an EuSe crystal, it is necessary to treat an Eu(II) ion and Se ion. Since both ions are unstable in the atmosphere, synthesis is required to be performed under high vacuum and at high temperatures (more than 1000° C.). However, it is difficult to obtain a nanosized crystal under these severe reaction conditions.

The inventors of the present invention have been devoted to research aimed at solving the aforementioned problem. As a result, they have discovered an Eu(III) complex that is stable in the atmosphere and have conceived a method for easily manufacturing a nanosized EuSe crystal.

Means for Solving the Problem

The manufacturing method of a nanosized EuSe crystal according to the present invention developed as just described is a manufacturing method of a nanosized EuSe crystal, wherein an Eu(III) complex is heated to obtain a nanosized EuSe crystal having a particle size corresponding to a heating condition, the Eu(III) complex being represented by the following general formula:

where n represents 1, 2, 3 or 4; X is selected from an oxygen atom, a sulfur atom, a selenium atom, and a tellurium atom; and $R_1$ and $R_2$ are identical or different, and are selected from aromatic groups, derivatives of aromatic groups, $C_1$-$C_{20}$ alkyl groups with saturated or unsaturated bonds, derivatives of $C_1$-$C_{20}$ alkyl groups with saturated or unsaturated bonds, a hydroxyl group, a nitro group, an amino group, a sulfonyl group, a cyano group, a silyl group, a phosphonic acid group, a diazo group, a mercapto group, and halogen atoms.

In the manufacturing method of a nanosized EuSe crystal according to the present invention, a mixture composed of the Eu(III) complex, and a counter cation and/or a solvent preferably may be heated to obtain a nanosized EuSe crystal having a particle size corresponding to the heating condition.

For the Eu(III) complex, an Eu(III) complex represented by a composition formula of $[Eu(Se_2PPh_2)_4]^-$ may be preferably used.

For the counter cation, $PPh_4^+$ may be preferably used.

Effects of the Invention

With the manufacturing method of a nanosized EuSe crystal according to the present invention, it is possible to manufacture the nanosized EuSe crystal, which has been considered impossible to be manufactured, in a very simple manner.

The reaction temperature of the Eu(III) complex according to the present invention is low (for example, the reaction temperature of $[Eu(Se_2PPh_2)_4]^-$ is approximately within a range from 50 to 500° C.) compared to that required in the conventional manufacturing process (approximately 1000° C.). Therefore, this allows a mass production of EuSe at low cost.

It is known that the absorption wavelength of an EuSe crystal is determined by the crystal's particle size (refer to Non-Patent Document 1 for example). However, in the manufacturing method of an EuSe crystal according to the present invention, since the particle size of a crystal can be controlled by the beating condition, it is possible to easily obtain a nanosized EuSe crystal to fit the purpose. In addition, as described earlier, the control of the heating temperature is effortless because the Eu(III) complex according to the present invention has a low reaction temperature. Hence, it is possible to minutely control the EuSe crystal's particle size.

With the method for manufacturing a nanosized EuSe crystal by heating a mixture composed of the Eu(III) complex, and a counter cation and/or a solvent, the Eu(III) complex is stabilized, which promotes ease in handling the materials in manufacturing a nanosized EuSe crystal.

Since nanosized EuSe crystals can be uniformly dispersed in various media, it is possible to create a variety of functional materials such as plastic and glass.

BEST MODE FOR CARRYING OUT THE INVENTION

Hereinafter, the manufacturing method of an EuSe nanocrystal according to the present invention will be described in detail. In the manufacturing method of a nanosized EuSe crystal according to the present invention, an Eu(III) complex is used as a raw material and is represented by the following general formula:

where n represents 1, 2, 3 or 4; X is selected from an oxygen atom, a sulfur atom, a selenium atom, and a tellurium atom; and R$_1$ and R$_2$ are mutually identical or different, and are selected from aromatic groups (for example, a phenyl group, a naphthyl group, and a tolyl group), derivatives of aromatic groups, C$_1$-C$_{20}$ alkyl groups with saturated or unsaturated bonds (for example, a methyl group, a methylene group, an ethyl group, an ethylene group, a propyl group, a propylene group, a butyl group, and a pentyl group), derivatives of C$_1$-C$_{20}$ alkyl groups with saturated or unsaturated bonds, a hydroxyl group, a nitro group, an amino group, a sulfonyl group, a cyano group, a silyl group, a phosphonic acid group, a diazo group, a mercapto group, and halogen atoms. The "alkyl groups" in the present invention may have one or more unsaturated bonds. Preferably R$_1$ and R$_2$ to be selected may not undesirably decrease the stability of the Eu(III), which is a precursor of the EuSe crystal. For example, they may be unlikely to undergo a structural change at temperatures below 100° C.

Such Eu(III) complex is easy to handle since it is stable even in the atmosphere.

Heating the Eu(III) complex under a predetermined heating condition produces a nanosized EuSe crystal. The heating condition is determined using temperature and time as the parameters. As the heating temperature increases and the reaction time becomes longer, the particle size of the nanosized EuSe crystal (i.e. the EuSe crystals' average particle size) created becomes larger. The size of the EuSe crystal which can be obtained in this manner can be controlled at will from below one nanometer to several hundred nanometers.

In the present invention, as a preferable Eu(III) complex, the Eu(III) complex whose composition formula is represented by [Eu(Se$_2$PPh$_2$)$_4$]$^-$ and the structural formula is represented by the following formula may be used:

In addition, in order to make the manufacture of the nanosized EuSe crystal easier, a mixture including a counter cation and/or a solvent in addition to the Eu(III) complex according to the present invention may be heated.

In the present invention, the counter cation may not be specifically limited but may be freely selected as long as it can be bound to an Eu(III) complex and the charges are balanced. Any type of cation may be used such as an organic cation and metal cation. For example, as the counter cation, PPh$_4^+$ whose structural formula is represented by the following formula may be used:

PPh$_4^+$ is very effective in stabilizing an Eu(III) complex in the atmosphere. In addition, since PPh$_4^+$ is an organic cation, it has an advantage in that it is difficult to get into the EuSe crystal as an impurity compared to metal cations.

The solvent is not specifically limited as long as it can dissolve the Eu(III) complex and the counter cation. The solvent can be a substance which is solid at room temperature and can be melted by heat. For example, hexadecylamine (HDA), tri-n-octylphosphine oxide (TOPO), ethylene glycol, and decahydronaphthalene can be used as the solvent. These solvents have the advantage that the reaction temperature can be as high as approximately 400° C. HDA and TOPO have a further advantage in that, after the crystallization of EuSe, these solvents are adsorbed onto the surface of the crystal and protect the crystal particle as a surface active agent.

If a counter cation and solvent are used as just described, each EuSe crystal particle generated may be naturally surface-modified in some cases. As is conventionally known, since the properties of an EuSe particle (the solubility to various solvents, etc) changes in accordance with the quality of the surface modifier, the counter cation and solvent may preferably be selected by taking account of the effect of the surface modification.

EXAMPLE

Hereinafter, an example of manufacturing a nanosized EuSe crystal performed by the inventors of the present invention will be described.

(Synthesis of Ligand (KSe$_2$PPh$_2$): Method 1 (FIG. 1))

Figure 1:
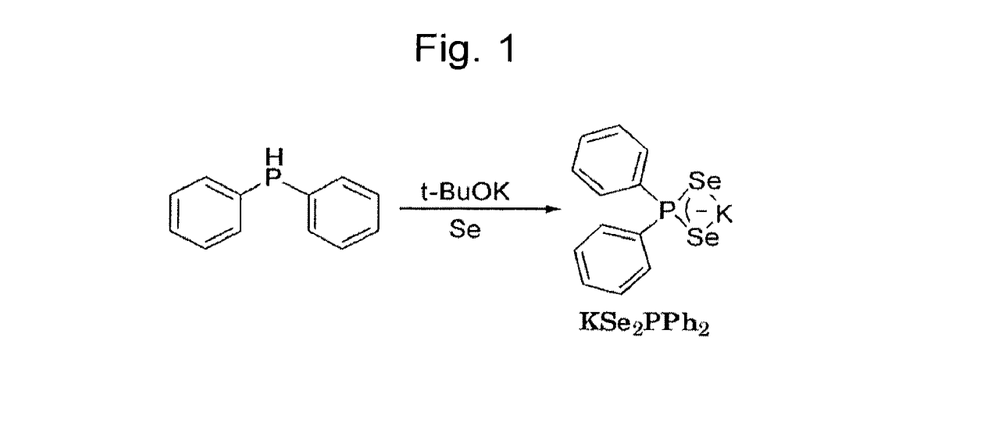
FIG. 1 is a reaction formula illustrating the first method of the synthesis of a ligand ($KSe_2PPh_2$)

Potassium tert-butoxide (t-BuOK) (1.18 g, 11.0 mmol), dehydrated tetrahydrofuran (THF) (100 mL), and diphenylphosphine (PPh$_2$H) (1.86 g, 10.0 mmol) were added into a four-necked recovery flask under Ar atmosphere. The color of the solution was red. Agitation was performed for two hours at room temperature. After that, selenium powder (1.58 g, 20 mmol) was added and agitation was performed for five hours at room temperature, which changed the color of the solution to yellow. After the reaction, the reaction mother liquor was filtered in order to remove the unreacted Se. Subsequently the filtrate was concentrated, and a reprecipitation was performed with n-hexane to separate a white solid, which was filtered through a funnel to recover. The approximate yield was 2.82 g and the approximate yield rate was 73.8%.

(Synthesis of Ligand (KSe$_2$PPh$_2$): Method 2 (FIG. 2))

Figure 2:
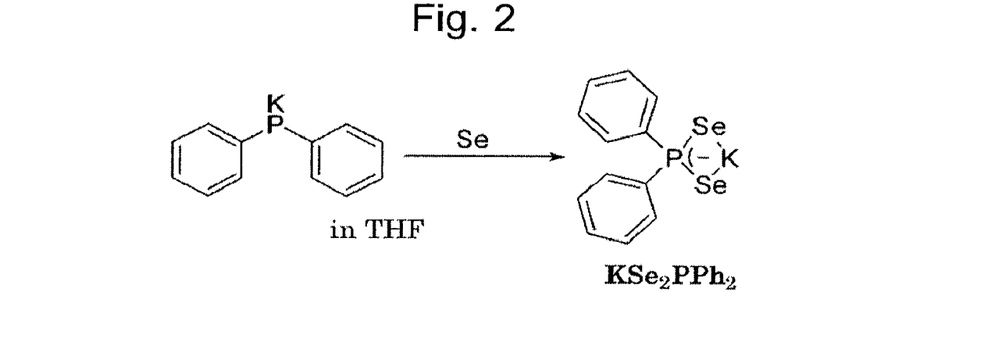
FIG. 2 is a reaction formula illustrating the second method of the synthesis of a ligand ($KSe_2PPh_2$)

50 mL (25 mmol) of KPPh$_2$ (potassium diphenylphosphide 0.5N in THF) and 2.2 equivalent amount of Se (55 mmol, 4.3 g) were added into a four-necked recovery flask under Ar atmosphere and agitation was performed for three hours. The color of the solution obtained was yellow. After the reaction, the reaction mother liquor was filtered in order to remove the unreacted Se. Subsequently, the filtrate was concentrated, and a reprecipitation was performed with n-hexane to separate a white solid, which was filtered through a funnel to recover. The approximate yield was 8.04 g and the approximate yield rate was 84.2%

The structural validation of the white solids obtained as just described was performed by $^1$H, $^{13}$C, and $^{31}$P NMR. The result was the following:

$^1$H NMR (300 MHz, d$_6$-DMSO, TMS) δ (ppm): 8.02 (m, PC$_6$H$_5$, 4H, Fr), 7.24 (m, PC$_6$H$_5$, 6H, H$^a$, H$^b$)

$^{13}$C NMR (75 MHz, d$_6$-DMSO, TMS) δ (ppm): 130.87, 130.72, 128.30, 128.25, 126.77, 126.61 $^{31}$P NMR (161.84 MHz, d$_6$-DMSO) δ (ppm): 24.02 (s+d satellites, $^1J_{PSe}$=−649 Hz)

The mass-to-charge ratio obtained as a result of an electrospray ionization (ESI) measurement was 344.878 m/z, which was in extremely favorable agreement with the mass-to-charge ratio of KSe$_2$PPh$_2$, 344.89 m/z.

In addition, the result obtained by an elemental analysis was the following:

Elemental analysis for C$_{12}$H$_{10}$KPSe Anal. Calc. (%) C, 37.71; H, 2.64; N, 0.00, found C, 36.75; H, 2.66; N, 0.14.

From these results, the white solid was presumed to be KSe$_2$PPh$_2$.

(Synthesis of Ligand (PPh$_4$Se$_2$PPh$_2$): (FIG. 3))

Figure 3:
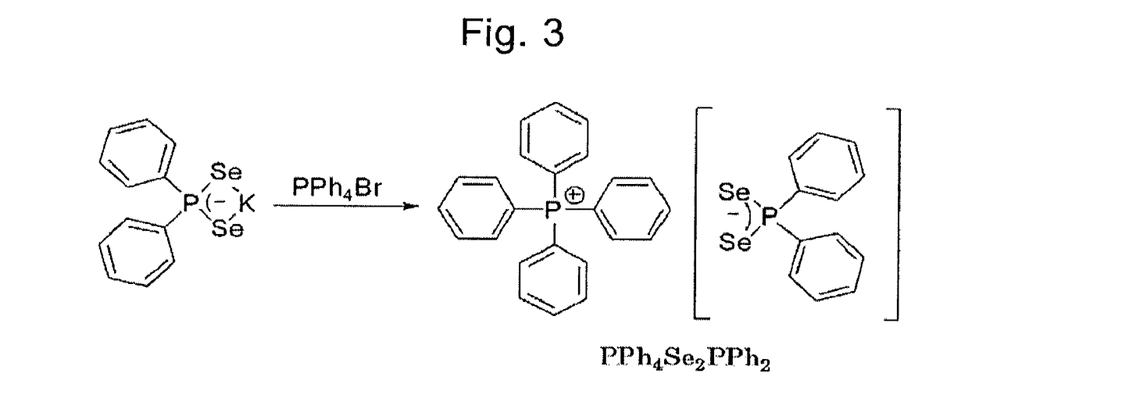
FIG. 3 is a reaction formula illustrating the synthesis of a ligand ($PPh_4Se_2PPh_2$).

A solution of KSe$_2$PPh$_2$ (1.54 g, 4.0 mmol) in MeOH and a solution of Ph$_4$PBr (1.69 g, 4.0 mmol) in MeOH were mixed and agitated overnight, and a yellow solid that had been precipitated was filtered through a funnel to recover (2.75 g). The solid was dissolved in CHCl$_3$ and separated with water two times to remove KBr. After that, the CHCl$_3$ solution was concentrated and reprecipitated into n-hexane to recover a yellow solid. The yield was 2.30 g and the yield rate was 83.9%.

The structural validation of the yellow solid obtained as just described was performed by H and $^{13}$C NMR. The result was the following:

$^1$H NMR (300 MHz, d$_6$-DMSO, TMS) δ (ppm): 7.82 (m, PC$_6$H$_5$, 24H, H$^c$, H$^d$, H$^e$, H$^f$)) 7.26 (m, PC$_6$H$_5$, 6H, H$^a$, H$^b$)

$^{13}$C NMR (75 MHz, d$_6$-DMSO, TMS) δ (ppm): 135.4, 135.3, 134.7, 134.5, 130.9, 130.7, 130.5, 130.4, 128.3, 128.2, 126.8, 126.6, 118.3, 117.1

The mass-to-charge ratio obtained by the ESI measurement (negative mode) was 344.777 m/z, which was in favorable agreement with the mass-to-charge ratio of PPh$_4$Se$_2$PPh$_2$, 344.89 m/z. Furthermore, The value of 339.058 m/z was obtained as the result of the ESI measurement (positive mode), which was in extremely favorable agreement with 339.13 m/z of PPh$_4$.

In addition, the result obtained by an elemental analysis was the following:

Elemental analysis for C$_{36}$H$_{30}$P$_2$Se$_2$ Anal. Calc. (%) C, 63.21; H, 4.43; N, 0.00, found C, 62.43; H, 4.28; N, 0.05.

From these results, the yellow solid was presumed to be PPh$_4$Se$_2$PPh$_2$.

Figure 4:
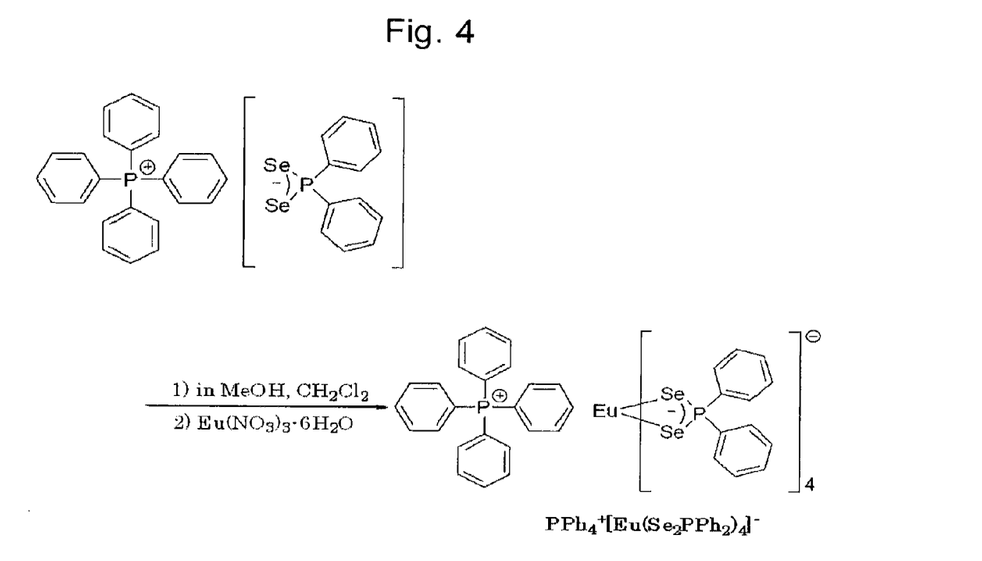
FIG. 4 is a reaction formula illustrating the synthesis of an Eu complex (PPh$_4^+$[Eu(Se$_2$PPh$_2$)$_4$]$^-$).

(Synthesis of Eu Complex (PPh$_4$$^+$[Eu(Se$_2$PPh$_2$)$_4$]$^-$) (FIG. 4))

Ph$_4$Se$_2$PPh$_2$(1.0 g, 1.46 mmol) was dissolved in the mixed solution of MeOH and CH$_2$Cl$_2$. Then, the solution of Eu(NO$_3$)$_3$. 6H$_2$O (0.22 g, 0.49 mmol) dissolved in MeOH in advance was added to it to react for four hours at 60° C. After the reaction, a filtering was performed and the filtrate was concentrated to obtain a yellow solid. Since the absorption band of a yellow crystal originates from the metal to ligand charge transfer (MLCT) of Eu and Se, this was confirmed to be PPh$_4$$^+$[Eu(Se$_2$PPh$_2$)$_4$]$^-$ (counter cation: PPh$_4$$^+$, Eu(III) complex: [Eu(Se$_2$PPh$_2$)$_4$]$^-$) (see FIG. 4).

(Synthesis of EuSe Crystal (FIG. 5))

Figure 5:
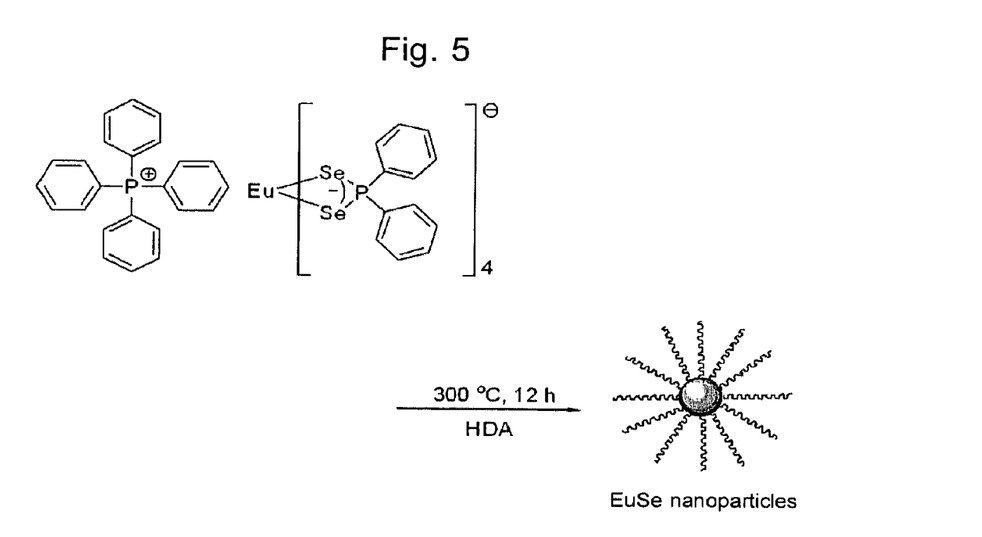
FIG. 5 is a reaction formula illustrating the synthesis of an EuSe crystal.

A reactor was deaerated and substituted by nitrogen, and a yellow Eu complex (PPh$_4$$^+$[Eu(Se$_2$PPh$_2$)$_4$]$^-$) was added to 11 g of HDA as a solvent (HDA is solid at room temperature and goes into a liquid state by heating). Then it was heated from room temperature to 300° C. and was agitated for two hours. After the reaction, it was diluted with n-hexane and cleansed with n-hexane and MeOH by a centrifuge to obtain a blue powder.

(Identification of EuSe Crystal)

Figure 6:
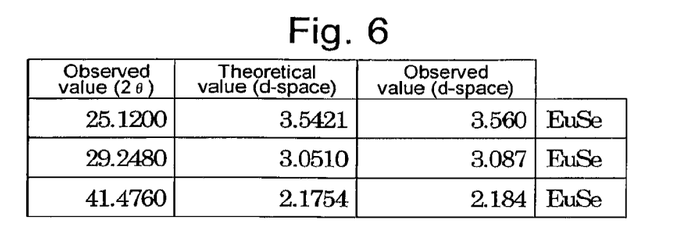
FIG. 6 is a chart of an X-ray diffraction measurement result.

The X-ray diffraction (XRD) measurement for the blue powder obtained as just described was performed and they were deduced to be EuSe crystals as a result. FIG. 6 illustrates the chart of the X-ray diffraction measurement result.

Figure 7:
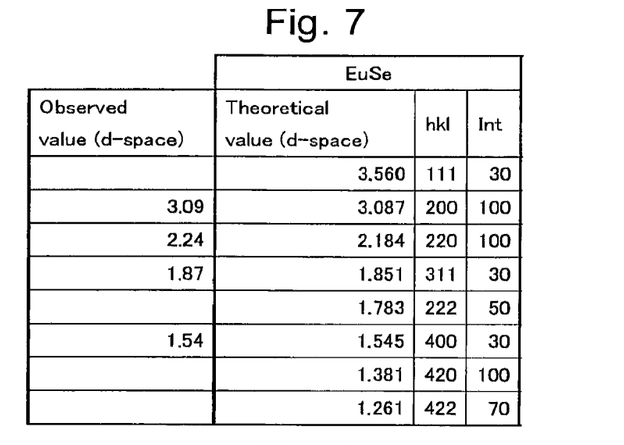
FIG. 7 is a measurement result chart of an electron diffraction pattern.

The measurement of the blue powder's electron diffraction pattern confirmed the existence of EuSe as a monocrystal. The measurement result chart of an electron diffraction pattern is illustrated in FIG. 7.

Figure 8:
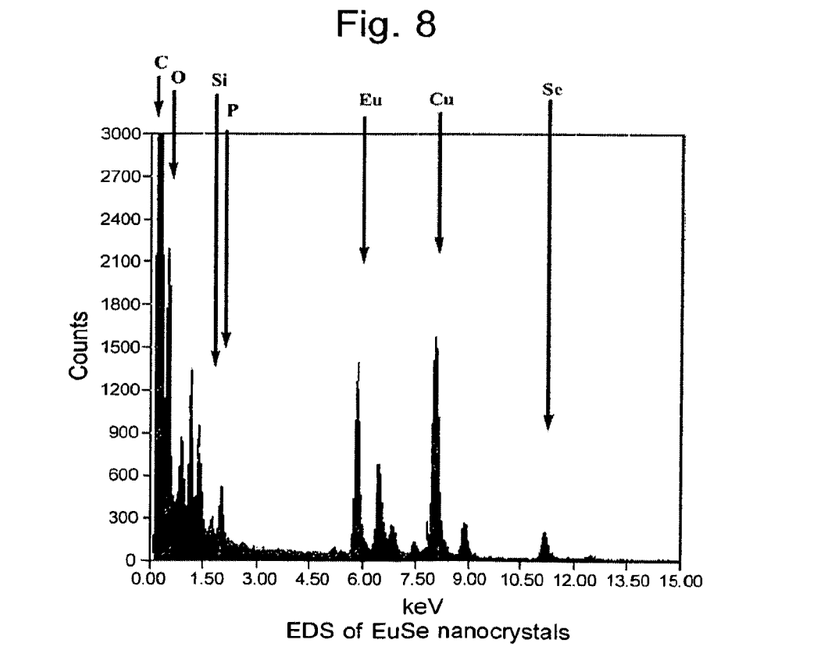
FIG. 8 is a graph illustrating an EDS measurement result for a blue powder (EuSe crystals).

In addition, the blue powder's element distribution was observed using an energy-dispersive X-ray spectroscopy (EDS), and as illustrated in FIG. 8, this confirmed that Eu and Se were included (Eu:Se=56:44).

Figure 9:
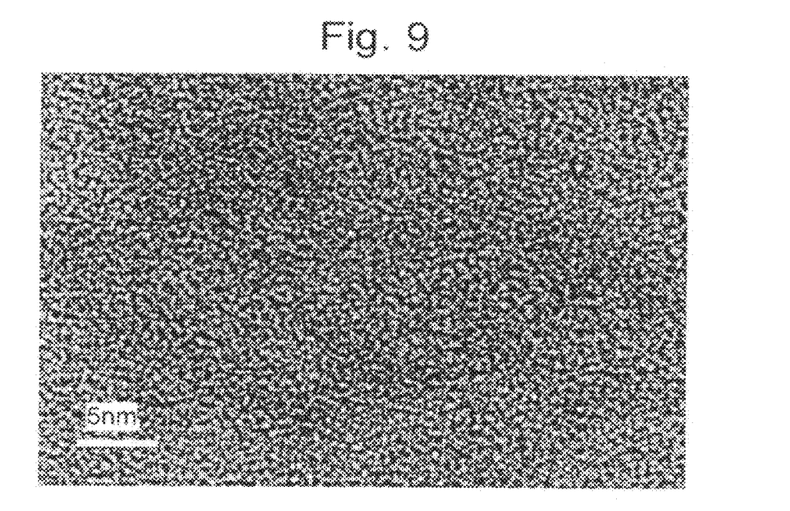
FIG. 9 illustrates a TEM image of a blue powder (EuSe crystals).

The blue powder was observed using a transmission electron microscope (TEM), and a clear stripe pattern was recognized as illustrated in FIG. 9, which also confirmed the existence of EuSe as a monocrystal.

Figure 10:
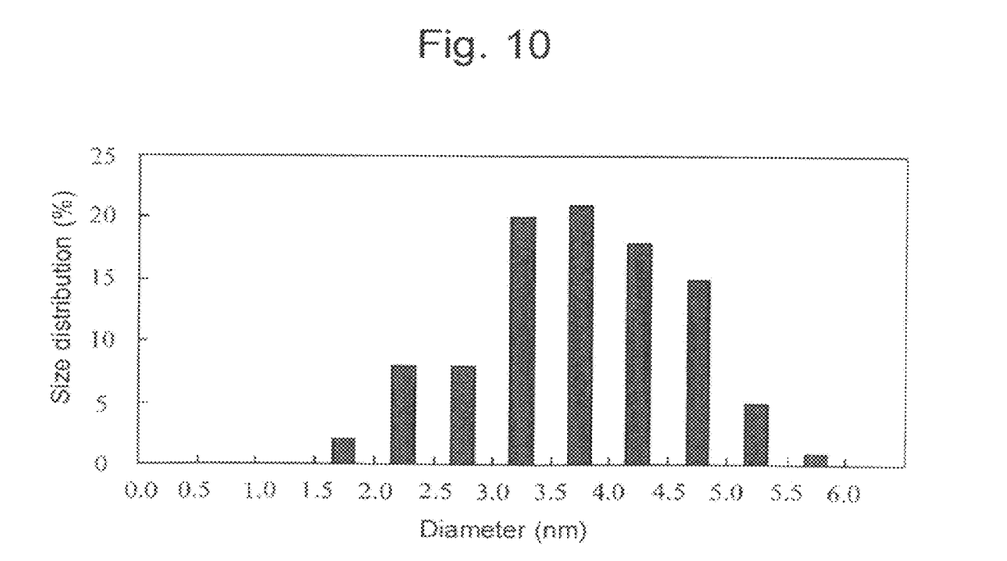
FIG. 10 illustrates a particle size distribution chart of EuSe crystals.

The particle size distribution of EuSe crystals was measured based on the TEM image illustrated in FIG. 9. The result obtained was as illustrated in FIG. 10, which confirmed that the particle size distribution range was approximately between 1 to 6 nm. The average particle size was 3.8 nm.

INDUSTRIAL APPLICABILITY

Since the EuSe crystals according to the present invention have a high dispersibility, they may be uniformly dispersed at a predetermined concentration in a variety of matrix resin raw materials and then the matrix resin may be polymerized, which produces magnetooptic-responsive plastic having excellent magnetooptical properties. The manufacturing process may use a conventionally-known manufacturing method, as described in Patent Document 1 for example, of magnetooptic-responsive plastic containing EuO crystals and EuS crystals. Of course, the medium in which the crystals are dispersed may be glass other than plastic (resin).

As the transparent matrix resin having a preferable optical transparency for manufacturing magnetooptic-responsive plastic, the following substances may be used for example: polyimide, polyamide, polymethyl methacrylate, polyacrylate, polyester, polyurethane, polycarbonate, epoxy resin, polystyrene, siloxane polymer, halide or deuteride of these, and resin in which two or more of these are mixed.

The magnetooptic-responsive plastic obtained in this manner exhibits the Faraday effect in accordance with the nanosized EuSe crystal's particle size, quantity, and surface modifier, at room temperature and additionally over a wide range between the ultraviolet region and infrared region. As described earlier, the EuSe crystal's Faraday effect is higher than that of the plastic using EuO crystals or EuS crystals. Therefore, with the magnetooptic-responsive plastic using the nanosized EuSe crystal according to the present invention, it is possible to create an optical isolator which is smaller and lighter than before.

In addition, it is easily possible to create a magnetooptical disk capable of writing and reading data, using the Kerr effect, in which the reflected light's polarizing direction rotates, which EuSe has.

The inventors of the present invention have carried out the following experiment in order to show that the nanosized EuSe crystal according to the present invention has excellent magnetooptical properties.

The solution in which $(PPh_4^+)(Se_2P(C_6H_5)_2)$ (0.30 g, 0.44 mmol) was dissolved in acetonitrile was added under nitrogen atmosphere to the solution in which $Eu(NO_3)_3 \cdot 6H_2O$ (0.20 g, 0.44 mmol) was dissolved in acetonitrile, and was agitated for ten minutes. Then it was added to HDA at 330° C. under nitrogen atmosphere. After four hours, it was cooled to room temperature and cleansed with n-hexane by a centrifuge to obtain a white powder.

Figure 11:
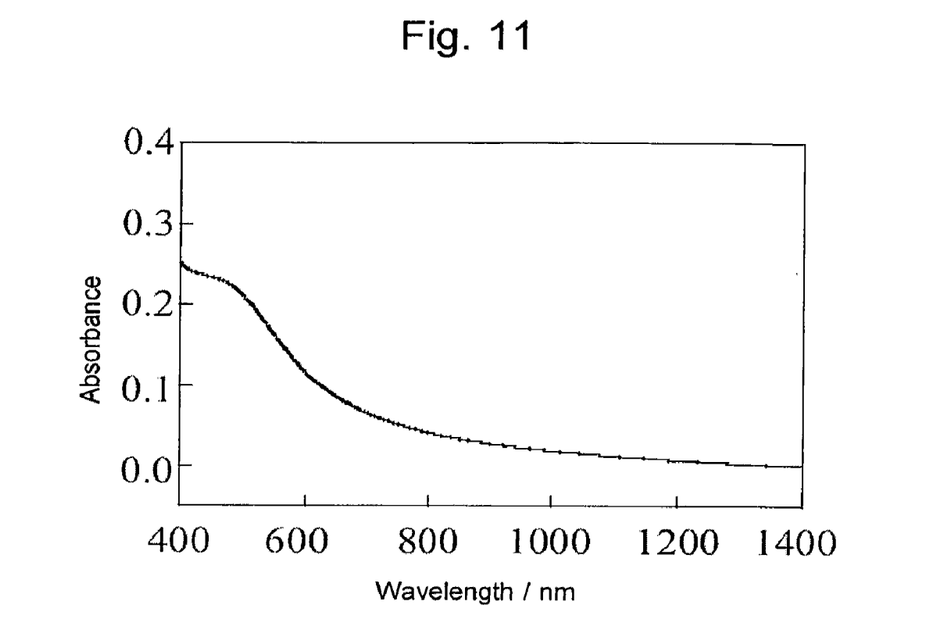
FIG. 11 illustrates an absorption spectrum of an EuSe-containing PMMA thin film in the ultraviolet and visible region.
Figure 12:
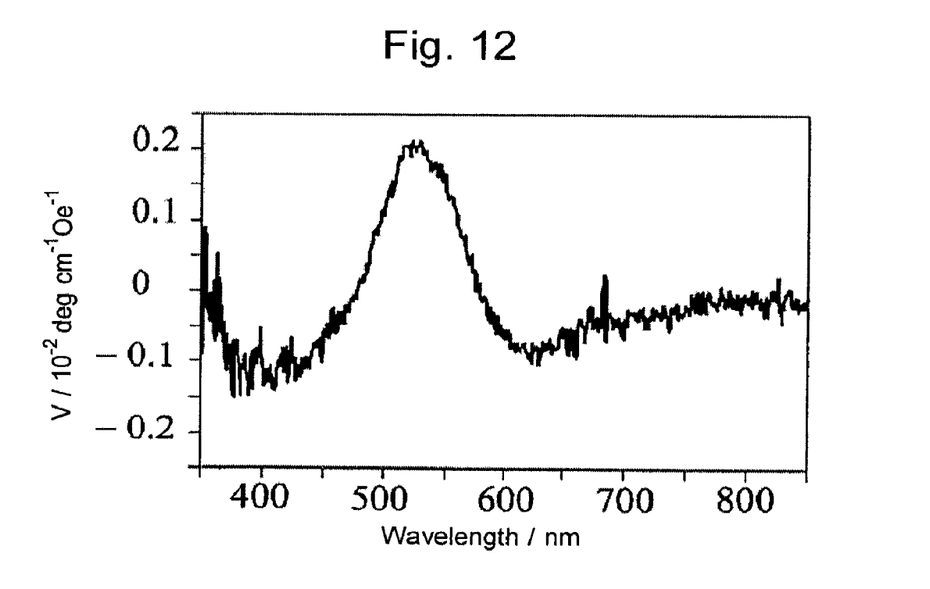
FIG. 12 illustrates a Faraday measurement spectrum of an EuSe-containing PMMA thin film.

The white powder of EuSe obtained as just described was dispersed in PMMA to create an EuSe-containing PMMA thin film. The thin film's thickness was 7.4 μm, and the concentration of EuSe in the thin film was not more than 5w %. The absorption spectrum of this thin film in the ultraviolet and visible region is illustrated in FIG. 11. Since the 4f-5d transition of Eu(II) is generally observed in the visible light region, it is thought that the electron transition process of nanosized EuSe crystal is due to the f4-5d transition. The Faraday measurement spectrum of this EuSe nanocrystals-containing PMMA thin film is illustrated in FIG. 12. The Verdet constant was 0.0021(deg.cm$^{-1}$.Oe$^{-1}$).

For comparison, an EuS nanocrystals-dispersed thin film whose density was the same as that of the aforementioned EuSe nanocrystals-containing PMMA thin film was prepared and the Verdet constant was measured. The result was 0.0003 (deg.cm$^{-1}$.Oe$^{-1}$). This result confirmed that the thin film containing the nanosized EuSe crystals according to the present invention has a higher magnetooptic constant (Verdet constant) than that of thin films including the known nanosized EuS crystals.

Thus far, the nanosized EuSe crystal and the manufacturing method of the nanosized EuSe crystal according to the present invention were described using examples. It should be noted that these are an example and that modification and improvement can be properly made within the spirit of the present invention as a matter of course.

The invention claimed is:

1. A manufacturing method of a nanosized EuSe crystal, the method comprising:
   heating an Eu(III) complex in a temperature range of equal to or more than 100° C. to be decomposed to generate an Eu(II) ion and an Se ion; and
   binding the Eu(II) ion and the Se ion to obtain a nanosized EuSe crystal having a particle size corresponding to a heating condition, wherein
   the Eu(III) complex is represented by a following general formula:

where n represents 1, 2, 3 or 4;
   X is selected from an oxygen atom, a sulfur atom, a selenium atom, and a tellurium atom; and
   $R_1$ and $R_2$ are identical or different, and are selected from aromatic groups, derivatives of aromatic groups, $C_1$-$C_{20}$ alkyl groups with saturated or unsaturated bonds, derivatives of $C_1$-$C_{20}$ alkyl groups with saturated or unsaturated bonds, a hydroxyl group, a nitro group, an amino group, a sulfonyl group, a cyano group, a silyl group, a phosphonic acid group, a diazo group, a mercapto group, and halogen atoms.

2. A manufacturing method of a nanosized EuSe crystal, the method comprising:
   heating a mixture composed of the Eu(III) complex according to claim 1, a counter cation, and a solvent in a temperature range of equal to or more than 100° C. to be decomposed to generate an Eu(II) ion and an Se ion; and
   binding the Eu(II) ion and the Se ion to obtain a nanosized EuSe crystal having a particle size corresponding to a heating condition.

3. The manufacturing method of a nanosized EuSe crystal according to claim 2, wherein the counter cation is $PPh_4^+$.

4. The manufacturing method of a nanosized EuSe crystal according to claim 2, wherein the Eu(III) complex is represented by a composition formula of $[Eu(Se_2PPh_2)_4]^-$.

5. The manufacturing method of a nanosized EuSe crystal according to claim 4, wherein the counter cation is $PPh_4^+$.

6. The manufacturing method of a nanosized EuSe crystal according to claim 1, wherein the Eu(III) complex is represented by a composition formula of $[Eu(Se_2PPh_2)_4]^-$.

7. A manufacturing method of a nanosized EuSe crystal, the method comprising:
   synthesizing $PPh_4Se_2PPh_2$ from $KSe_2PPh_2$;
   synthesizing $PPh_4^+[Eu(Se_2PPh_2)_4]^-$ from the $PPh_4Se_2PPh_2$;
   heating the $PPh_4^+[Eu(Se_2PPh_2)_4]^-$ in a temperature range of equal to or more than 100° C. to be decomposed to generate an Eu(II) ion and an Se ion; and
   binding the Eu(II) ion and the Se ion to obtain a nanosized EuSe crystal having a particle size corresponding to a heating condition.

8. An Eu(III) complex represented by a following general formula:

where n represents 1, 2, 3 or 4;
X is selected from an oxygen atom, a sulfur atom, a selenium atom, and a tellurium atom; and
$R_1$ and $R_2$ are identical or different, and are selected from aromatic groups, derivatives of aromatic groups, $C_1$-$C_{20}$ alkyl groups with saturated or unsaturated bonds, derivatives of $C_1$-$C_{20}$ alkyl groups with saturated or unsaturated bond, a hydroxyl group, a nitro group, an amino group, a sulfonyl group, a cyano group, a silyl group, a phosphonic acid group, a diazo group, a mercapto group, and halogen atoms.

* * * * *